US012806166B2

(12) United States Patent
Oh et al.

(10) Patent No.: US 12,806,166 B2
(45) Date of Patent: Nov. 24, 2026

(54) PHARMACEUTICAL COMPOSITION CONTAINING MACROLIDE COMPOUND, PRODUCTION METHOD THEREFOR, AND METHOD USING SAME

(71) Applicants: SEOUL NATIONAL UNIVERSITY R&DB FOUNDATION, Seoul (KR); INDUSTRY-ACADEMIC COOPERATION FOUNDATION GYEONGSANG NATIONAL UNIVERSITY, Gyeongsangnam-do (KR); THE INDUSTRY & ACADEMIC COOPERATION IN CHUNGNAM NATIONAL UNIVERSITY (IAC), Yuseong-gu (KR)

(72) Inventors: Dong-Chan Oh, Seoul (KR); Sunghoon Hwang, Seoul (KR); Jongheon Shin, Seoul (KR); Eun Kyeong Jo, Daejeon (KR); Ji Chan Jang, Seoul (KR)

(73) Assignees: SEOUL NATIONAL UNIVERSITY R&DB FOUNDATION, Seoul (KR); INDUSTRY- ACADEMIC COOPERATION FOUNDATION GYEONGSANG NATIONAL UNIVERSITY, Gyeongsangnam-do (KR); THE INDUSTRY & ACADEMIC COOPERATION IN CHUNGNAM NATIONAL UNIVERSITY (IAC), Yuseong-gu (KR)

( * ) Notice: Subject to any disclaimer, the term of this patent is extended or adjusted under 35 U.S.C. 154(b) by 1069 days.

(21) Appl. No.: 17/904,187

(22) PCT Filed: Sep. 29, 2020

(86) PCT No.: PCT/KR2020/013335
§ 371 (c)(1),
(2) Date: Aug. 12, 2022

(87) PCT Pub. No.: WO2021/162196
PCT Pub. Date: Aug. 19, 2021

(65) Prior Publication Data

US 2023/0094006 A1 Mar. 30, 2023

(30) Foreign Application Priority Data

Feb. 14, 2020 (KR) ........................ 10-2020-0018558

(51) Int. Cl.
*A61K 31/335* (2006.01)
*A61P 31/06* (2006.01)
*A61P 31/10* (2006.01)

(52) U.S. Cl.
CPC ............ *A61K 31/335* (2013.01); *A61P 31/06* (2018.01); *A61P 31/10* (2018.01)

(58) Field of Classification Search
CPC ...... A61K 31/335; A61K 31/365; A61P 31/06
See application file for complete search history.

(56) References Cited

U.S. PATENT DOCUMENTS

| | | | |
|---|---|---|---|
| 7,071,170 | B2 | 7/2006 | Kaneko |
| 9,090,667 | B2 | 7/2015 | Kim et al. |
| 2015/0210729 | A1 | 7/2015 | Baurin et al. |
| 2020/0010499 | A1 | 1/2020 | Winqvist et al. |

FOREIGN PATENT DOCUMENTS

| | | | |
|---|---|---|---|
| KR | 10-2014-0114522 | A | 9/2014 |
| KR | 10-2015-0056569 | A | 5/2015 |
| KR | 20150144812 | A | 12/2015 |
| KR | 10-2018-0090113 | A | 8/2018 |
| WO | 2019/020767 | A1 | 1/2019 |
| WO | 2021/162196 | A1 | 8/2021 |

OTHER PUBLICATIONS

English translation of selected portions of "A Study of the Massive Procution and the Development of Novel Therapeutic Agents From Maine Microbial Bioantive Natural Products By Biotechnological Methods" (Year: 2025).*

"WHO consolidated guidelines on tuberculosis: Tuberculosis preventive treatment" (2020), retrieved from who.int on Jan. 9, 2025. (Year: 2020).*

Vasiliu et al., "Tuberculosis prevention: current strategies and future directions," Clin. Microbiol. Infect. 2024;30(9):1123-30. PMID: 37918510. (Year: 2024).*

<Tetrahedron Letters> No. 56, pp.6693-6695, Sunagawa et al., Synthetic study of arenicolide C: stereoselective synthesis of the C19-C36 segment.

Application No. CN202080096560.5, Office Action, mailed on Jul. 22, 2023, 8 pages (No English translation available).

Doucet-Populaire, F. et al., "Natural and Acquired Macrolide Resistance in Mycobacteria," *Current Drug Target—Infectious Disorders*. 2002, vol. 2, pp. 355-370.

Final Report on the Mass Production of Marine Microorganisms Originating Physiological Active Natural Products and the Development of New Drug Materials Using Biotechnology Methods. Published Jul. 20, 2020, non-official translation, See pp. 89-90, 126-134, 138 and 147 and figure 80.

Panchanathan Manivasagan et al., "Pharmaceutically active secondary metabolites of marine actinobacteria," Microbiological Research 169 (2014) pp. 262-278.

(Continued)

*Primary Examiner* — Theodore R. Howell
(74) *Attorney, Agent, or Firm* — Kilpatrick Townsend & Stockton LLP

(57) ABSTRACT

A pharmaceutical composition or a health functional food including a macrolide compound, a method of preparing the same, and a method using the same may be used to prevent or treat *Mycobacterium* sp. bacterial infection, such as tuberculosis, Hansen's disease, and non-tuberculous *Mycobacterium* sp. bacterial infections, or symptoms related thereto.

14 Claims, 8 Drawing Sheets

(56) References Cited

OTHER PUBLICATIONS

Williams et al., "Arenicolides A-C, 26-Membered Ring Macrolides from the Marine Actinomycete *Salinispora arenicola*," Journal of Organic Chemistry, Jul. 6, 2007; 72(14): 5025-5034. Doi:10.1021/jo061878x.
Zhu, Z.J. et al., "Structure-activity relationships of macrolides against *Mycobacterium tuberculosis*," Tuberculosis. 2008, vol. 8, pp. S49-S63. See abstract, pp. S50-S51 and Figures 1-2.
International Search Report and Written Opinion for PCT/KR2020/013335 mailed May 10, 2021, 4 pages.
Request for the Submission of an Opinion for KR appln No. 10-2020-0018558 dated Jun. 28, 2021, all pages.
Written Decision on Registration for KR 10-2020-0018558 dated Sep. 3, 2021, all pages.

* cited by examiner

PHARMACEUTICAL COMPOSITION CONTAINING MACROLIDE COMPOUND, PRODUCTION METHOD THEREFOR, AND METHOD USING SAME

STATEMENT AS TO INVENTIONS MADE UNDER SPONSORED RESEARCH AND DEVELOPMENT GRANTS

This work was supported by the National Research Foundation of Korea (NRF) grant funded by the Korea government (MSIT) (RS-2026-25501101).

TECHNICAL FIELD

The present disclosure relates to a pharmaceutical composition including a macrolide compound, a method of preparing the same, and a method using the same.

BACKGROUND ART

Bioactive substances derived from microorganisms have largely been a source of antibacterial, antifungal, and anticancer drugs, and have been developed as new drugs for the treatment of various diseases including the same, or have become a template for the development of new drugs. However, the physiological activity of many of the microorganism-derived compounds has not yet been revealed. For example, arenicolides A to C have been isolated from marine actinomycetes, but their physiological activities have not yet been elucidated (Journal of Organic Chemistry, 2007, vol. 72, no. 14, pp. 5025-5034).

Tuberculosis (TB) is an infectious disease that has existed for a long time such that traces of it are even found in Stone Age relics from around 7,000 BC. Despite being an age-old disease, tuberculosis is still the leading cause of death among young people worldwide. *Mycobacterium tuberculosis*, the cause of tuberculosis, was discovered in 1882 by the German bacteriologist Robert Koch. Not all people who are infected with *Mycobacterium tuberculosis* develop tuberculosis, but tuberculosis develops when the immune system is weakened after the body is infected. *Mycobacterium tuberculosis* has a slower growth rate compared to general infectious bacteria, but it is characterized by exhibiting resistance to various drugs by mutating while surviving even in macrophages. Therefore, as a method of treating tuberculosis, it is difficult to see a therapeutic effect with a general single-drug prescription, and long-term treatment with a combination of various drugs is recommended.

Various compounds such as isoniazid, rifampicin, ethambutol, pyrazinamide, streptomycin, and kanamycin are used as anti-tuberculosis agents. However, isoniazid may cause peripheral neuritis, rifampicin may cause thrombocytopenia, streptomycin may cause balance disorders, hearing loss, or peripheral neuropathy, ethambutol may cause visual impairment, and pyrazinamide may cause hyperuricacidemia. As such, there is an issue that the number of prescriptions or the dosage is limited because of the limited variety of anti-tuberculosis therapeutic agents and the various side effects of each drug. In addition, compounds having anti-tuberculosis activity are being developed (Korean Patent Publication No. 10-2015-0144812 (2015.12.28)).

Therefore, there is a need to select a new anti-tuberculosis agent having anti-tuberculosis activity and few side effects.

DESCRIPTION OF EMBODIMENTS

Technical Problem

Provided is a pharmaceutical composition for preventing or treating bacterial infection or symptoms related thereto, including a macrolide compound, a stereoisomer, a solvate, or a pharmaceutically acceptable salt thereof.

Provided are a strain producing the compound, or the stereoisomer, solvate, or pharmaceutically acceptable salt thereof, and a method of preparing a pharmaceutical composition including the same.

Provided is a health functional food for preventing or ameliorating *Mycobacterium* sp. bacterial infection or symptoms related thereto, including the compound, or the stereoisomer, solvate, or pharmaceutically acceptable salt thereof.

Provided is a method of preventing or treating *Mycobacterium* sp. bacterial infection or symptoms related thereto by using the pharmaceutical composition.

Solution to Problem

As aspect provides a pharmaceutical composition for preventing or treating *Mycobacterium* sp. bacterial infection or symptoms related thereto, including a compound represented by Formula 1, a stereoisomer, a solvate, or a pharmaceutically acceptable salt thereof:

Formula 1

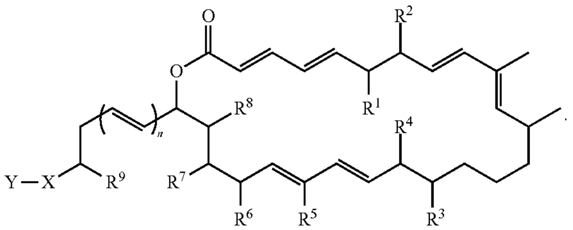

$R^1$ in Formula 1 may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^1$ may be a hydroxyl group or a substituted or unsubstituted $C_1$ to $C_{20}$ alkoxy group. $R^1$ may be a $C_1$ to $C_{20}$, $C_1$ to $C_{15}$, $C_1$ to $C_{10}$, $C_1$ to $C_5$, or $C_1$ to $C_2$ alkoxy group. $R^1$ is, for example, a methoxy group.

In Formula 1, $R^2$ may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^2$ may be a hydroxyl group or a substituted or unsubstituted $C_1$ to $C_{20}$ alkoxy group. $R^2$ is, for example, a hydroxyl group.

In Formula 1, $R^3$ may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^3$ may be a hydroxyl group or a substituted or unsubstituted $C_1$ to $C_{20}$ alkoxy group. $R^3$ may be a $C_1$ to $C_{20}$, $C_1$ to $C_{15}$, $C_1$ to $C_{10}$, $C_1$ to $C_5$, or $C_1$ to $C_2$ alkoxy group. $R^3$ is, for example, a methoxy group.

In Formula 1, $R^4$ may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^4$ may be a hydroxyl group or a substituted or unsubstituted $C_1$ to $C_{20}$ alkoxy group. $R^4$ is, for example, a hydroxyl group.

In Formula 1, $R^5$ may be hydrogen, a hydroxyl group, an amino group, a halogen group, a cyano group, $—C(=O)R_a$, $—C(=O)OR_a$, $—OCO(OR_a)$, $—C=N(R_a)$, $—SR_a$, $—S(=O)R_a$, $—S(=O)_2R_a$, $—PR_a$, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof. $R_a$ means a substituent, and may be hydrogen, a $C_1$ to $C_{10}$ alkyl group, or a $C_6$ to $C_{20}$ aryl group. $R^5$ may be a substituted or unsubstituted $C_1$ to $C_{20}$ alkyl group. $R^5$ is, for example, a methyl group.

In Formula 1, $R^6$ may be hydrogen, a hydroxyl group, an amino group, a halogen group, a cyano group, $—C(=O)R_a$, $—C(=O)OR_a$, $—OCO(OR_a)$, $—C=N(R_a)$, $—SR_a$, $—S(=O)R_a$, $—S(=O)_2R_a$, $—PR_a$, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof. $R_a$ means a substituent, and may be hydrogen, a $C_1$ to $C_{10}$ alkyl group, or a $C_6$ to $C_{20}$ aryl group. $R^6$ may be a substituted or unsubstituted $C_1$ to $C_{20}$ alkyl group. $R^6$ is, for example, a methyl group.

In Formula 1, $R^7$ may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^7$ may be a hydroxyl group or a substituted or unsubstituted $C_1$ to $C_{20}$ alkoxy group. $R^7$ is, for example, a hydroxyl group.

In Formula 1, $R^8$ may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^8$ may be a hydroxyl group or a substituted or unsubstituted $C_1$ to $C_{20}$ alkoxy group. $R^8$ may be a $C_1$ to $C_{20}$, $C_1$ to $C_{15}$, $C_1$ to $C_{10}$, $C_1$ to $C_5$, or $C_1$ to $C_2$ alkoxy group. $R^8$ is, for example, a methoxy group.

In Formula 1, $R^9$ may be one selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof. $R^9$ may be a hydroxyl group or a substituted or unsubstituted $C_1$ to $C_{20}$ alkoxy group. $R^9$ is, for example, a hydroxyl group.

In Formula 1, at least one of $R^1$, $R^3$, and $R^8$ may be a substituted or unsubstituted $C_1$ to $C_{10}$ alkoxy group. One, two, or all of $R^1$, $R^3$, and $R^8$ are, for example, a methoxy group.

In Formula 1, at least one of $R^2$, $R^4$, $R^7$ and $R^9$ may be a hydroxyl group. One, two, three or all of $R^2$, $R^4$, $R^7$ and $R^9$ are, for example, a hydroxyl group.

In Formula 1, one or both of $R^5$ and $R^6$ may be a methyl group.

In Formula 1, the structure marked with parentheses indicates that an alkyl group and an alkenyl group are alternately repeated one or more times. n represents the number of times an alkyl group and an alkenyl group are alternately repeated. n may be an integer from 1 to 20. For example, n is 1.

In Formula 1, X may be a substituted or unsubstituted 3-membered to 10-membered heterocyclic group containing one or more oxygen atoms. The heterocyclic ring group may be substituted with a hydroxyl group, a $C_1$ to $C_{10}$ alkyl group, a $C_1$ to $C_{10}$ alkoxy group, or a combination thereof. The heterocyclic ring group may be an ethylene oxide group or tetrahydrofuran.

In Formula 1, Y may be a substituted or unsubstituted $C_1$ to $C_{30}$ alkyl group. The alkyl group may be substituted with one or more hydroxyl groups or $C_1$ to $C_{10}$ alkoxy groups.

The term "hydroxy" refers to a —OH functional group (hydroxyl group).

The term "amino" refers to an amine ($—NH_2$) group consisting of one nitrogen atom and two hydrogen atoms.

The term "halogen" atom includes fluorine, bromine, chlorine, iodine, and the like.

The term "ketone" refers to a functional group in which one carbonyl group is bonded to two hydrocarbon groups.

The term "cyano" refers to a functional group consisting of a triple bond between a carbon atom and a nitrogen atom.

The term "substituted" in the "substituted or unsubstituted" refers to being introduced in place of a hydrogen atom when a derivative is formed by substituting one or more hydrogen atoms in an organic compound with another atomic group, and a substituent refers to the introduced atomic group. The substituent may be a halogen atom, a hydroxyl group, a nitro group, a cyano group, an amino group, an amidino group, an acetamino group, hydrazine, hydrazone, a carboxyl group, a sulfonyl group, a sulfamoyl group, a sulfonic acid group, phosphoric acid, $C_1$ to $C_5$ alkyl group, $C_1$ to $C_5$ alkoxy group, $C_2$ to $C_5$ alkenyl group, $C_2$ to $C_5$ alkynyl group, $C_3$ to $C_{10}$ cycloalkyl group, $C_6$ to $C_{10}$ aryl group, $C_6$ to $C_{10}$ heteroaryl group, $C_6$ to $C_{20}$ arylalkyl group, $C_6$ to $C_{20}$ heteroarylalkyl group, or a combination thereof.

The term "alkyl" refers to a fully saturated branched or unbranched (or straight-chain or linear) hydrocarbon. The alkyl may be a $C_1$ to $C_{20}$, $C_1$ to $C_{15}$, $C_1$ to $C_{10}$, or $C_1$ to $C_5$ alkyl group. The alkyl is, for example, methyl, ethyl, n-propyl, isopropyl, n-butyl, isobutyl, sec-butyl, n-pentyl, isopentyl, neopentyl, iso-amyl, n-hexyl, 3-methylhexyl, 2,2-dimethylpentyl, 2,3-dimethylpentyl, or n-heptyl.

The term "alkoxy" refers to an alkyl single bonded to an oxygen atom. The alkoxy is, for example, methoxy, ethoxy, or butoxy.

The term "alkenyl" refers to a branched or unbranched hydrocarbon having one or more carbon-carbon double bonds. The $C_2$ to $C_{20}$ alkenyl group may be a $C_2$ to $C_{15}$, $C_2$ to $C_{10}$, or $C_2$ to $C_5$ alkenyl group. The alkenyl group is, for example, vinyl, allyl, butenyl, isopropenyl, or isobutenyl.

The term "alkynyl" refers to a branched or unbranched hydrocarbon having at least one carbon-carbon triple bond. The $C_2$ to $C_{20}$ alkynyl group may be a $C_2$ to $C_{15}$, $C_2$ to $C_{10}$, or $C_2$ to $C_5$ alkynyl group. The alkynyl is, for example, ethynyl, butynyl, isobutynyl, or isopropynyl.

The term "alkylene oxide" refers to a cyclic group consisting of one oxygen atom and two or more carbon atoms.

The term "cycloalkyl" refers to a saturated or partially unsaturated non-aromatic monocyclic, bicyclic or tricyclic hydrocarbon group.

The term "aryl" refers to an aromatic system including one or more rings, which is used alone or in combination, and includes groups having an aromatic ring fused to one or more carbon rings. The $C_6$ to $C_{30}$ aryl group may be a $C_6$ to $C_{15}$, or $C_6$ to $C_{10}$ aryl group. The aryl is, for example, phenyl, naphthyl, or tetrahydronaphthyl.

The term "aryloxy" refers to an aryl group single bonded to an oxygen atom.

The term "heteroaryl" refers to a monocyclic or bicyclic organic compound containing one or more heteroatoms selected from the group consisting of N, O, P and S, and in which the remaining ring atoms are carbon. The heteroaryl group may include 1 to 5 heteroatoms, and 5 to 10 ring members. The S or N may be oxidized to have several oxidation states.

The term "heterocyclic ring" or "heterocyclic" group refers to a cyclic hydrocarbon containing at least one heteroatom. The heterocyclic ring group may contain 3 to 30, 3 to 20, 3 to 10, 3 to 6, or 3 to 5 members. Heterocyclic ring groups may contain one or more other heteroatoms in addition to the carbon atoms in the ring. The heteroatom may be any one or more selected from the group consisting of sulfur, nitrogen, oxygen and boron. The heterocyclic ring group is, for example, an ethylene oxide group or a tetrahydrofuran group.

The compound represented by Formula 1 may be represented by Formula 2 or Formula 3:

Formula 2

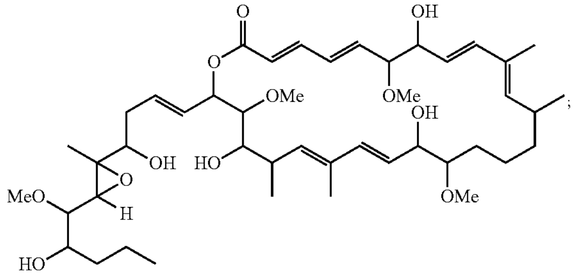

;

and

Formula 3

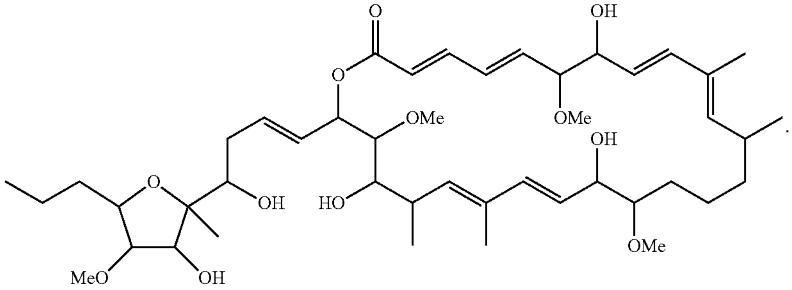

.

The compound represented by Formula 1 may be represented by Formula 4 or Formula 5:

Formula 4

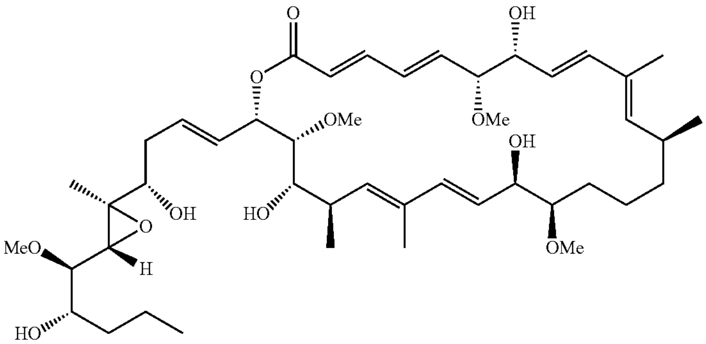

and;

Formula 5

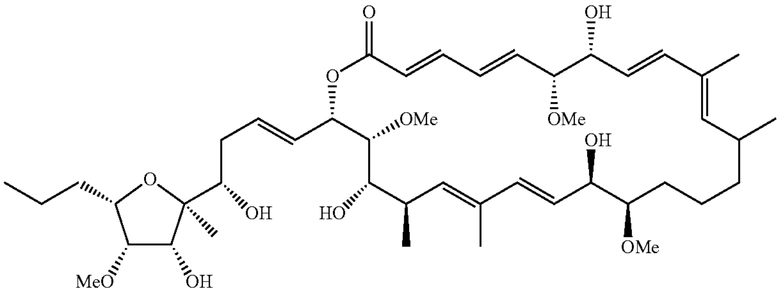

.

disease, and nontuberculous mycobacterial (NTM) infection. The tuberculosis may be multidrug resistance (MDR)

"Isomer" of the term "stereoisomer" refers to a compound that has the same molecular formula, but does not have the same mode of connection or spatial arrangement of constituent atoms in the molecule. Isomers include, for example, structural isomers, and stereoisomers. The stereoisomer may be a diasteromer or an enantiomer. An enantiomer refers to an isomer that does not overlap the mirror image as in the relationship between the left hand and the right hand, and is also called an optical isomer. Enantiomers are divided into R (Rectus: clockwise) and S (Sinister: counterclockwise) when 4 or more substituents differ from each other at the chiral center carbon. Diastereomers refer to stereoisomers that are not mirror images, and may be divided into cis-trans isomers resulting from different spatial arrangements of atoms.

The term "solvate" refers to a compound solvated in an organic or inorganic solvent. The solvate is, for example, a hydrate.

The term "salt" refers to inorganic and organic acid addition salts of a compound. The pharmaceutically acceptable salt may be a salt that does not cause serious irritation to the organism to which the compound is administered and does not impair the biological activity and properties of the compound. The inorganic acid salt may be hydrochloride, bromate, phosphate, sulfate, or disulfate. The organic acid salt may be formate, acetate, propionate, lactate, oxalate, tartrate, malate, maleate, citrate, fumarate, besylate, camsylate, edisilate, trichloroacetic acid, trifluoroacetate, benzoate, gluconate, methanesulfonate, glycolate, succinate, 4-toluenesulfonate, galacturonate, embonate, glutamate, ethanesulfonate, benzenesulfonate, p-toluenesulfonate, or aspartate. The metal salt may be a calcium salt, a sodium salt, a magnesium salt, a strontium salt, or a potassium salt.

The *Mycobacterium* sp. bacterial infection may be selected from the group consisting of tuberculosis, Hansen's or extensive drug resistance (XDR) tuberculosis. The multidrug resistance tuberculosis may be tuberculosis in which *Mycobacterium tuberculosis* does not die even when isoniazid and rifampicin are administered to the human body. Extensive drug resistance tuberculosis may be tuberculosis that is simultaneously resistant to isoniazid and rifampicin as well as to quinolones and injections.

The symptoms associated with the *Mycobacterium* sp. bacterial infection may be cough, chest pain, fever, chills, decreased appetite, weight loss, inflammation, or a combination thereof. For example, a symptom associated with *Mycobacterium* sp. bacterial infection may be inflammation induced by bacteria of the *Mycobacterium* genus.

The bacteria of the *Mycobacterium* genus are bacteria belonging to Corynebacterineae of Actinobacteria. Bacteria of the *Mycobacterium* genus may have acid-fast properties. The bacteria of the *Mycobacterium* genus may be *Mycobacterium tuberculosis*, nontuberculous mycobacteria, or *bacillus* Calmette-Guerin (BCG) strain. The bacteria of the *Mycobacterium* genus is, for example, *Mycobacterium tuberculosis, Mycobacterium bovis, Mycobacterium abscessus, Mycobacterium africanum, Mycobacterium microti, Mycobacterium leprae, Mycobacterium canetti, Mycobacterium avium, Mycobacterium kansasii*, and *Mycobacterium marinum.*

The term "prevention" refers to any action that suppresses a disease or delays the onset of a disease by administration of a composition. The term "treatment" refers to any act of improving or beneficially changing the symptoms of a disease by administering the composition.

The composition may further include an antibiotic. The antibiotic may be an anti-tuberculosis drug. The anti-tuberculosis drug is, for example, ethambutol, isoniazid, rifampicin, SQ-109, pyrazinamide, streptomycin, kanamycin, capreomycin, ethionamide, prothionamide, enviomycin, para-aminosalicylic acid, cycloserine, amikacin, levofloxacin, moxifloxacin, gatifloxacin, ofloxacin, terizidone, thionamide, ethionamide, prothionamide, clofazimine, linezolid, amoxicillin, clavulanate, thioacetazone, imipenem, cilastatin, clarithromycin, bedaquiline, delamanid, limipenem, cilastatin, meropenem, or a combination thereof. The compound represented by Formula 1, stereoisomer, solvate, or pharmaceutically acceptable salt thereof, and the antibiotic may be in a single composition or seperate compositions for simultaneous or sequential administrations.

The pharmaceutical composition may further include a carrier, an excipient or a diluent. Carriers, excipients and diluents may include, for example, lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, or mineral oil.

The pharmaceutical composition may be formulated as oral formulations such as powders, granules, tablets, capsules, suspensions, emulsions, syrups, and aerosols, or as external preparations, suppositories, or sterilized solutions for injection. In the formulation, the pharmaceutical composition may be prepared by using a diluent or excipient such as a filler, a thickening agent, a binder, a wetting agent, a disintegrant, or a surfactant.

In the pharmaceutical composition, solid formulations for oral administration may be tablets, pills, powders, granules, or capsules. The solid formulation may further include an excipient. The excipient may be, for example, starch, calcium carbonate, sucrose, lactose, or gelatin. In addition, the solid formulation may further comprise a lubricant such as magnesium stearate, or talc. In the pharmaceutical composition, liquid formulations for oral administration may be a suspension, oral liquids, an emulsion, or a syrup. The liquid formulation may contain water or liquid paraffin. The liquid formulation may include an excipient, for example, a wetting agent, a sweetener, a fragrance, or a preservative. In the pharmaceutical composition, formulations for parenteral administration may be sterile aqueous solutions, non-aqueous solvents, suspensions, emulsions, lyophilized preparations, or suppositories. The non-aqueous solvents or the suspensions may include, vegetable oil or ester. The vegetable oil may be, for example, propylene glycol, polyethylene glycol, or olive oil. The ester may be, for example, ethyl oleate. The base of the suppository may be witepsol, macrogol, tween 61, cacao butter, laurin fat, or glycerogelatin.

The effective amount of the pharmaceutical composition may vary depending upon the subject's condition and body weight, severity of the disease, formulation of the drug, route and duration of administration, etc., and may be appropriately selected by those skilled in the art. However, the compound, isomer, derivative, solvate, or pharmaceutically acceptable salt thereof may be administered in an amount of, for example, about 0.0001 mg/kg to about 100 mg/kg, or about 0.001 mg/kg to about 100 mg/kg, 1 to 24 times a day, or 1 to 7 times in 2 days or a week, or 1 to 24 times in 1 month to 12 months. In the pharmaceutical composition, the compound, isomer, derivative, solvate, or pharmaceutically acceptable salt thereof may be present in an amount of from about 0.0001 wt % to about 10 wt %, or from about 0.001 wt % to about 1 wt %, with respect to the total weight of the composition.

The administration may be oral, or parenteral administration. The administration may be via, for example, oral, percutaneous, subcutaneous, rectal, intravenous, intra-arterial, intraperitoneal, intramuscular, intrasternal, local, intranasal, intratracheal, or intradermal route. The composition may be administered systemically or locally, and the composition may be administered alone or in combination with other pharmaceutically active compounds.

Another aspect provides a *Micromonospora* sp. GR10 strain (Accession No.: KCTC14124BP) for producing the compound, or the stereoisomer, solvate, or pharmaceutically acceptable salt thereof according to an aspect.

The compound, stereoisomer, solvate, and pharmaceutically acceptable salt are as described above.

The strain includes variants thereof. A variant may be, for example, a variant generated by natural mutation or artificial mutation. Artificial mutations may be caused by physical mutagens such as ultraviolet rays, or chemical mutagens such as basic compounds.

The strain includes spores, cells, or cultures of the strain.

Another aspect provides a method of manufacturing a pharmaceutical composition including a compound represented by Formula 1, a stereoisomer, a solvate, or a pharmaceutically acceptable salt thereof, the method including: culturing *Micromonospora* sp. GR10 strain (accession number: KCTC14124BP); and isolating the compound, or the stereoisomer, solvate, or pharmaceutically acceptable salt thereof according to an aspect from the culture of the strain.

The compound, stereoisomer, solvate, pharmaceutically acceptable salt, pharmaceutical composition, and GR10 strain of the *Micromonospora* genus are as described above.

The method includes culturing *Micromonospora* sp. GR10 strain (accession number: KCTC14124BP). The culturing may be culturing the strain in a liquid medium or a solid medium. The medium may contain, for example, glucose, starch syrup, dextrin, starch, molasses, animal oil, or vegetable oil as a carbon source. The medium may contain, for example, bran, soybean meal, wheat, malt, cottonseed meal, fish meal, corn steep liquor, broth, yeast extract, ammonium sulfate, sodium nitrate, or urea as a nitrogen source.

The culturing may be with shaking or stationary under aerobic conditions. The incubation temperature may be, for example, from about 20° C. to about 40° C., from about 25° C. to about 37° C., from about 28° C. to about 35° C., or about 30° C. The incubation time may be, for example, from about 1 day to about 4 months, from about 1 day to about 2 months, from about 1 day to about 6 weeks, from about 1 day to about 1 month, from about 1 day to about 2 weeks, or about 1 day to about 1 week.

The method includes isolating the compound represented by Formula 1, or the stereoisomer, solvate, or pharmaceutically acceptable salt thereof from the culture.

The isolation may include performing concentration, centrifugation, filtration, or chromatography of the culture medium. The chromatography may be, for example, column chromatography, planar chromatography, paper chromatography or thin film chromatography depending on the type of stationary phase. The chromatography may be, for example, gas chromatography, liquid chromatography, or affinity chromatography, depending on the physical properties of the mobile phase. The liquid chromatography may be, for example, high performance liquid chromatography (HPLC). The chromatography may be, for example, ion exchange chromatography, size-exclusion chromatography, depending on the separation method. The chromatography may be, for example, normal phase chromatography or reverse phase chromatography.

Another aspect provides a health functional food for preventing or ameliorating *Mycobacterium* sp. bacterial infection or symptoms related thereto, including the compound, or the stereoisomer, solvate, or pharmaceutically acceptable salt thereof.

The compound, stereoisomer, solvate, salt, *Mycobacterium* sp. bacterial infection or symptoms related thereto, and prevention are as described above.

The term "amelioration" includes any action that causes the symptoms of a disease to be improved or to be beneficial.

The health functional food may be used as a functional food or added to various foods by formulating the compound represented by Formula 1, the stereoisomer, solvate, or salt thereof into a capsule, powder, suspension, etc. The food is, for example, meat, sausage, bread, chocolate, candy, snacks, confectionery, pizza, ramen, other noodles, gum, dairy products including ice cream, various soups, beverages, tea, drinks, alcoholic beverages, vitamin complex, functional food and health food.

Another aspect provides a method of preventing or treating *Mycobacterium* sp. bacterial infection or symptoms related thereto, including administering to a subject a pharmaceutical composition according to an aspect.

The pharmaceutical composition, *Mycobacterium* sp. bacterial infection or related symptoms, prevention, and treatment are as described above.

The subject may be a mammal, such as a human, mouse, rat, cow, horse, pig, dog, monkey, sheep, goat or cat. The subject may be suffering from, or highly likely to suffer from *Mycobacterium* sp. bacterial infection or symptoms related thereto.

The method may further include administering an antibiotic to the subject. The antibiotic may be administered to the subject simultaneously, separately, or sequentially with the compound represented by Formula 1, or the stereoisomer, solvate, or pharmaceutically acceptable salt thereof.

The administration may be oral, or parenteral administration. The administration may be via, for example, an oral, percutaneous, subcutaneous, rectal, intravenous, intra-arterial, intraperitoneal, intramuscular, intrasternal, local, intranasal, intratracheal, or intradermal route. The pharmaceutical composition may be administered systemically or locally, and the composition may be administered alone or in combination with other pharmaceutically active compounds.

The effective amount of the pharmaceutical composition may vary depending upon the patient's condition and body weight, severity of the disease, formulation of the drug, route and duration of administration, etc., and may be appropriately selected by those skilled in the art. The dosage may be, for example, in the range of from about 0.001 mg/kg to about 100 mg/kg, from about 0.01 mg/kg to about 10 mg/kg, or from about 0.1 mg/kg to about 1 mg/kg for an adult. The administration may be administered once a day, multiple times a day, multiple times a week, once a week, once every 2 weeks, once every 3 weeks, or once every 4 weeks to once a year.

Advantageous Effects of Disclosure

A pharmaceutical composition or a health functional food including arenicolide, a macrolide compound, a method of preparing the same, and a method using the same may be used to prevent or treat *Mycobacterium* sp. bacterial infection, such as tuberculosis, Hansen's disease, and non-tuberculous *Mycobacterium* sp. bacterial infections, or symptoms associated thereto.

MODE OF DISCLOSURE

Hereinafter, the disclosure will be described in more detail through embodiments. However, these embodiments are intended to illustrate the present disclosure, and the scope of the present disclosure is not limited to these embodiments.

Figure 1:
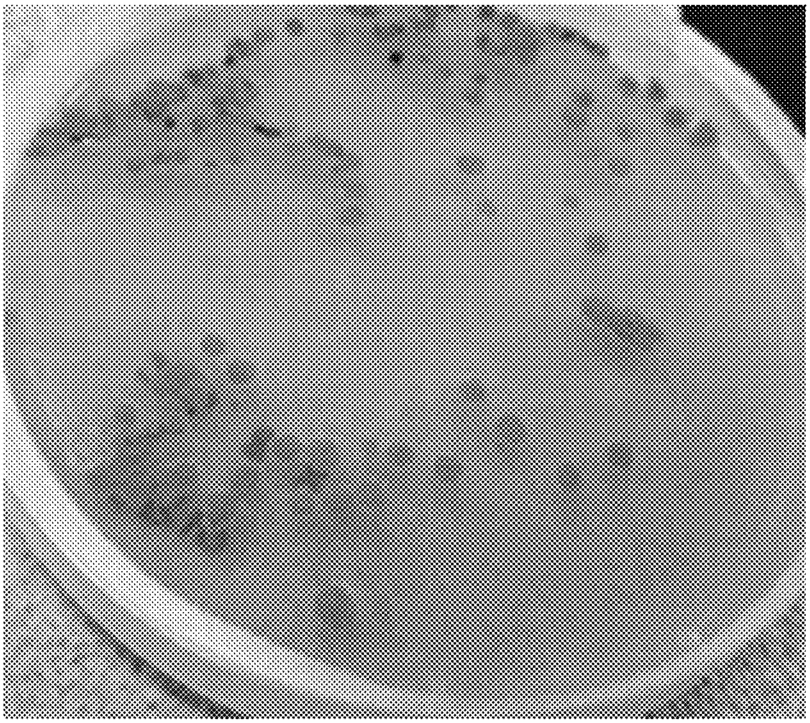
FIG. 1 is a photograph of a culture medium of *Micromonospora* sp. GR10 strain.

Example 1. Isolation of Arenicolide and Structural Identification 1-1. Isolation of Arenicolide-Producing Strains The arenicolide producing strain of GR10 strain was isolated from K solid medium (25 g of starch, 2 g of yeast extract, 15 g of soytone, 4 g of $CaCO_3$, and 20 g of agar per 1 L of distilled water) (FIG. 1).

The whole genome of GR10 strain was isolated and 16S ribosomal DNA was cloned by polymerase chain reaction (PCR), and the nucleic acid sequence was analyzed (SEQ ID NO: 1). Based on the results of 16S rDNA sequencing, the strain was identified as the *Micromonospora* genus. This strain was named *Micromonospora* sp. GR10 strain, and the strain was deposited to the Korea Research Institute of Bioscience and Biotechnology on Jan. 31, 2020 (Accession No.: KCTC14124BP).

1-2. Culture of GR10 Strain of *Micromonospora* Genus

The GR10 strain of the *Micromonospora* genus was spread on a sterile YEME solid medium (4 g of yeast extract, 10 g of malt extract, 4 g of glucose, and 20 g of agar per 1 L of distilled water) and cultured for 4 weeks at approximately 30° C.

The spores of the cultured GR10 strain were inoculated into 150 mL of modified K liquid medium (2 g yeast extract, 5 g malt extract, 5 g soytone, 5 g starch, 2 g starch, 5 g of mannitol, and 6 g of glycerol per 1 L distilled water), and cultured for about 7 days at 30° C., with shaking at 200 rpm. 5 mL of the culture medium was inoculated into a 200 mL volume of modified K liquid medium, and cultured for about 4 days under the conditions of 170 rpm and 30° C. Then, 10 mL of the culture medium was inoculated into a 1 L volume of modified K liquid medium, and cultured for about 7 days under the conditions of 170 rpm and 30° C.

1-3. Isolation and Purification of Arenicolide

The culture of the GR10 strain cultured in Example 1-2 was obtained.

1 L of the culture medium of the cultured GR10 strain and about 1 L volume of ethyl acetate (EtOAc, Daejeong Hwageum Co., Ltd.) were put into a separatory funnel mounted on a stand, then the funnel was closed with a stopper and shaken up, down, left and right for 1 minute to proceed the first extraction. After that, the funnel was mounted on a stand again, and after the water layer and the EtOAc layer were completely separated, the valve of the separatory funnel was opened to remove the water layer. Fresh EtOAc was added to the aqueous layer, and repeated extraction was performed in the same manner. The EtOAc layer was separately stored in a clean flask, and anhydrous sodium sulfate (Daejeong Hwageum Co., Ltd.) was added to remove the water remaining in the culture. The EtOAc layer from which the water was removed was transferred back to a 3 L round flask, and then dried under reduced pressure using a decompression dryer. A total of 50 L of the strain was cultured, and as a result of the extraction, about 10 g of crude extract was obtained.

High-performance liquid chromatography (HPLC) was used to purify arenicolide from the GR10 strain extract. The extract was dissolved in a sufficient amount of methanol (MeOH), and solid impurities were removed by using a syringe filter (ADVANTEC, 25HP045AN), and a purification process was proceeded by using preparative HPLC. For material purification, a reversed-phase column ($C_{18}$(2) Luna 10 μm 250×21.2 mm) was used, and a condition of a concentration gradient (flow rate: 10 mL/min, detection: UV 230 nm) of acetonitrile (ACN)/aqueous solution of 30% (v/v) to 70% (v/v) was used.

It was confirmed through liquid chromatography mass spectrometry (LC/MS) analysis that pure arenicolide A was eluted about 32 minutes after injection into HPLC under these conditions. Through repeated experiments, 250 mg of arenicolide A and 50 mg of arenicolide C were obtained from 10 g of extract.

1-4. Analysis of Physicochemical Properties of Arenicolide (1) Identification of Chemical Structure of Arenicolide A The structure of arenicolide A was identified based on 1 D and 2D nuclear magnetic resonance (NMR) spectra. For nuclear magnetic resonance spectra ($^1$H NMR, $^{13}$C NMR), 500 MHz NMR manufactured by Bruker was used, and DMSO-$d_6$ was used as the solvent.

The structural positioning of arenicolide A by nuclear magnetic resonance spectra is shown in Table 1.

[Arenicolide A]

(1) Molecular formula: $C_{45}H_{72}O_{12}$ (2) Molecular weight: 804

(3) Color: Transparent (4) $^1$H-NMR (DMSO-$d_6$, 600 MHz): see Table 1

(5) $^{13}$C-NMR (DMSO-$d_6$, 150 MHz): see Table 1

TABLE 1

| Position | $\delta_C$ | Type | $\delta_H$ | mult. (J in Hz) |
|---|---|---|---|---|
| 1 | 166.6 | C | | |
| 2 | 121.6 | CH | 5.95 | d (15.0) |
| 3 | 143.9 | CH | 7.23 | dd (15.0, 11.0) |
| 4 | 132.6 | CH | 6.39 | dd (15.0, 11.0) |
| 5 | 139.4 | CH | 5.84 | dd (15.0, 8.0) |
| 6 | 85.7 | CH | 3.58 | dd (8.0, 8.0) |
| 7 | 75.6 | CH | 3.96 | dd (8.0, 8.0) |
| 8 | 124.4 | CH | 5.32 | dd (15.0, 8.0) |
| 9 | 139.3 | CH | 6.15 | d (15.0) |

TABLE 1-continued

| Position | $\delta_C$ | Type | $\delta_H$ | mult. (J in Hz) |
|---|---|---|---|---|
| 10 | 131.5 | C | | |
| 11 | 140.2 | CH | 5.23 | d (9.0) |
| 12 | 32.3 | CH | 2.50 | m |
| 13 | 37.0 | $CH_2$ | 1.24 | m |
| 14 | 23.1 | $CH_2$ | 1.30 | m |
| 15 | 29.9 | $CH_2$ | 1.45 | m |
| 16 | 84.8 | CH | 3.05 | m |
| 17 | 74.6 | CH | 4.00 | dd (8.0, 5.0) |
| 18 | 127.4 | CH | 5.60 | dd (15.0, 8.0) |
| 19 | 136.6 | CH | 6.18 | d (15.0) |
| 20 | 133.0 | C | | |
| 21 | 135.2 | CH | 5.24 | d (9.0) |
| 22 | 36.6 | CH | 2.77 | m |
| 23 | 76.0 | CH | 3.29 | m |
| 24 | 82.7 | CH | 3.30 | m |
| 25 | 77.9 | CH | 5.39 | m |
| 26 | 127.6 | CH | 5.82 | m |
| 27 | 130.7 | CH | 5.81 | m |
| 28 | 36.2 | 1.30 | 2.34/2.16 | m |
| 29 | 76.1 | CH | 3.21 | dd (9.0, 3.0) |
| 30 | 61.9 | C | | |
| 31 | 62.2 | CH | 2.88 | d (9.0) |
| 32 | 83.1 | CH | 2.99 | dd (8.5, 5.5) |
| 33 | 71.0 | CH | 3.55 | m |
| 34 | 34.8 | $CH_2$ | 1.53/1.42 | m |
| 35 | 18.7 | $CH_2$ | 1.54/1.34 | m |
| 36 | 13.1 | $CH_3$ | 0.93 | t (7.0) |
| 37 | 55.9 | $CH_3$ | 3.30 | s |
| 38 | 11.6 | $CH_3$ | 1.68 | s |
| 39 | 19.7 | $CH_3$ | 0.94 | d (6.5) |
| 40 | 57.8 | $CH_3$ | 3.37 | s |
| 41 | 11.7 | $CH_3$ | 1.77 | s |
| 42 | 16.6 | $CH_3$ | 1.01 | d (7.0) |
| 43 | 59.4 | $CH_3$ | 3.38 | s |
| 44 | 12.2 | $CH_3$ | 1.29 | s |
| 45 | 57.5 | $CH_3$ | 3.44 | s |

(2) Identification of Three-Dimensional Structure of Arenicolide A

Most of the three-dimensional structure of arenicolide A was revealed in the paper in which arenicolide was first reported (Williams et al., J. Org. Chem. 2007, vol. 72, No. 14, pp. 5025-5034). In order to identify the three-dimensional structure of carbon 39, which has not yet been revealed, a new computational method, DP4 analysis, was used.

First, since the DP4 analysis method has a higher significance as the molecular weight is lowered, the chain portion, which is judged not to significantly affect the chemical shift of the substance, is excluded, and only the macrocyclic structure part was modeled through energy minimization by using the Avogadro 1.2.0. program, and molecular models having structures 39R and 39S were modeled. And, from among the many chemical forms searched through the stable chemical forms of each of the two models by using the Maestro program, only forms with a stable energy of 10 kJ/mol were selected. The weight of each chemical form was calculated by calculating Boltzmann population according to the relative energy of each of the selected forms. As a result, 8 chemical forms of the 39R model were determined and 36 forms of 39S were determined. Optimization of ground state geometrical structure was performed using each chemical model with the Turbomole X 4.3.2 program, and then, the chemical shift values in each chemical form of the obtained optimized structural models was deduced by calculation. By assigning weight to the models according to the Boltzmann population, the average chemical shift values were calculated. When comparing the chemical shift values revealed by actual experiments with the calculated chemical shift values of 39R and 39S models, the carbon chemical shift value was 96.7%, the hydrogen chemical shift value was 100.0%, and when the carbon and hydrogen values were combined, the chemical shift value was 100.0%, thus the three-dimensional structure of carbon 39 was confirmed to be S.

The chemical structural formula of arenicolide A analyzed from the nuclear magnetic resonance spectrum data and results of the three-dimensional structural analysis is shown below:

[Arenicolide A]

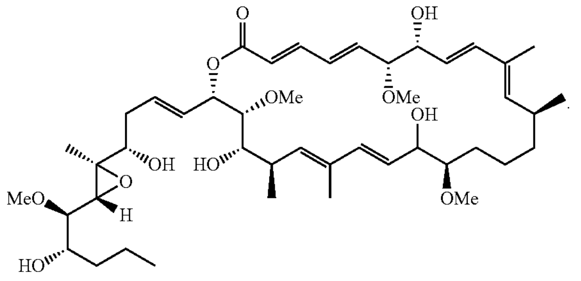

On the other hand, the chemical structural formula of arenicolide C is shown below:

[Arenicolide C]

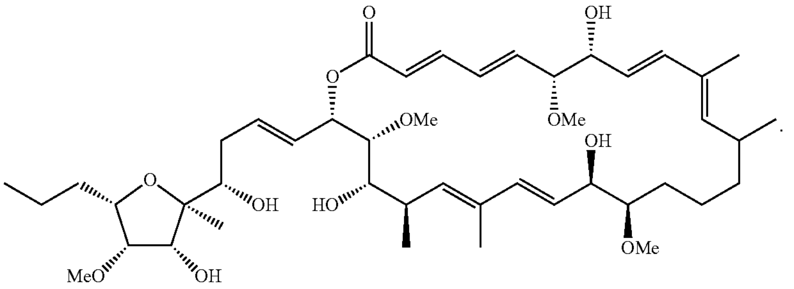

Figure 2A:
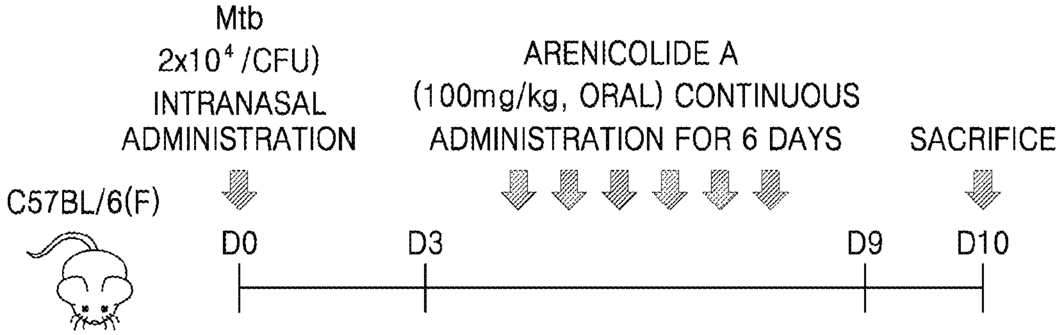
FIG. 2A is a schematic of a method for confirming the *Mycobacterium tuberculosis*-removing activity of arenicolide A.

Example 2. Confirmation of Anti-Mycobacterial Activity of Arenicolide 2-1. Confirmation of Anti-Tuberculosis Activity of Arenicolide C57BL/6 mice (n=16) were prepared to investigate the anti-tuberculous activity of arenicolide A. Mice were nasally infected with $2\times10^4$/CFU of *Mycobacterium tuberculosis* (Mtb), and the mice were randomly divided into two groups (each, n=8). From the 4th day, arenicolide A was orally administered at a dose of 100 mg/body weight kg for 6 days. Phosphate-buffered saline (PBS) was administered as a negative control. Mice were sacrificed on day 10 from the day of infection (FIG. 2A). The number of viable *Mycobacterium tuberculosis* in the lung tissue was investigated, and the results are shown in FIG. 2B (***: p<0.001).

Figure 2B:
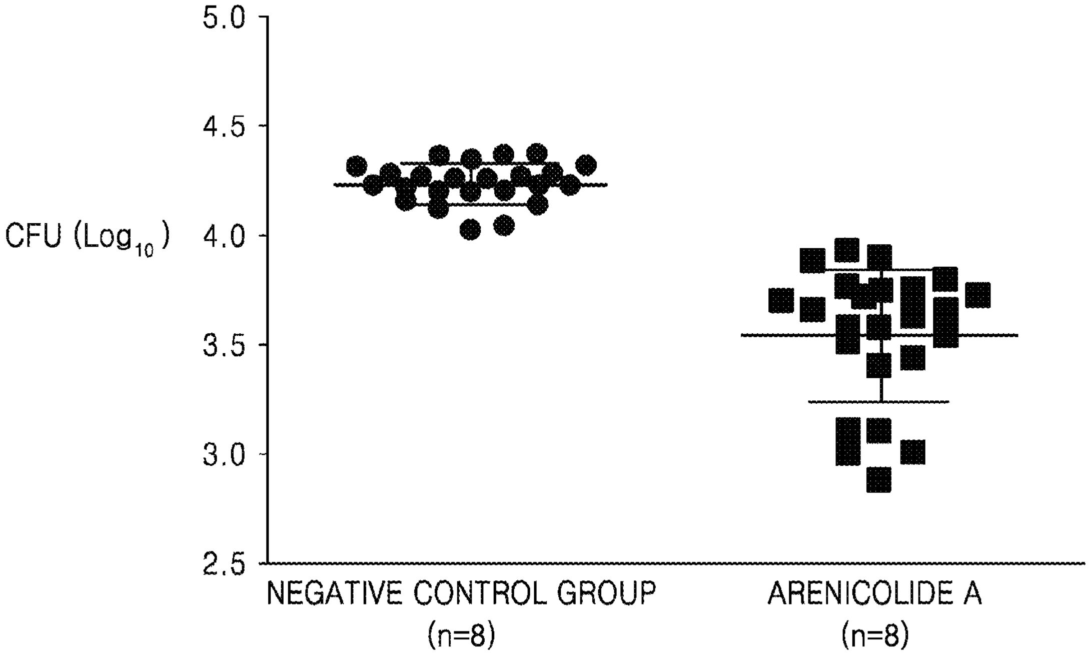
FIG. 2B is a graph showing the number of viable cells of *Mycobacterium tuberculosis* in lung tissue when arenicolide A is administered (CFU: colony forming unit)

As shown in FIG. 2B, the number of viable *Mycobacterium tuberculosis* in the lung tissue was significantly reduced in the group to which arenicolide A was orally administered compared to the negative control group. Therefore, it was confirmed that arenicolide A showed efficacy as a therapeutic candidate in a mouse tuberculosis infection model.

Figure 2C:
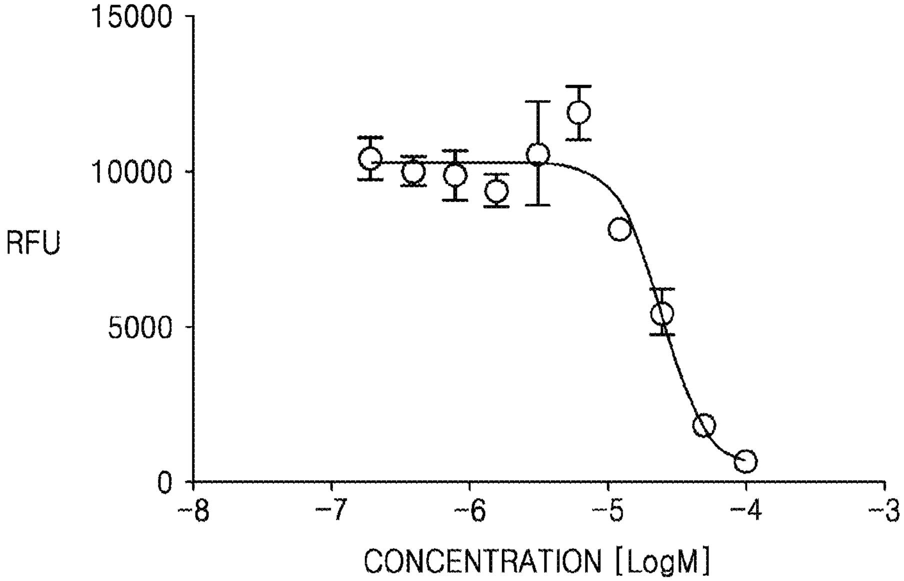
FIG. 2C is a dose response curve of arenicolide A for a tuberculosis strain (RFU: relative fluorescence unit).

To know the minimal inhibitory concentration (MIC) of arenicolide A, a dose-response curve (DRC) was calculated using the *M. tuberculosis* mc2 6230 strain. MIC was measured by using a resazurin microtiter assay (REMA). Briefly, 100 μl of 7H9 liquid medium was added to each well of a 96-well microtiter plate, and two-fold serial dilutions of antibiotics were directly added to each well. Plates were covered and incubated for 5 days at 37° C. Resazurin (0.01% (w/v)) was added to each well and the plates were incubated overnight. Fluorescence intensity was measured by using a SpectraMax M3 Multi-Mode Microplate Reader (Molecular Devices, CA, USA) (ex. 560/em. 590 nm). MIC values were calculated by using Prism 6 (GraphPad Software, Inc., La Jolla, CA), and the results are shown in FIG. 2C. As shown in FIG. 2C, the $MIC_{50}$ value of arenicolide A was about 24.6 μM.

On the other hand, as a result of measuring the anti-tuberculosis activity against *Mycobacterium tuberculosis* Mtb H37Rv strain (standard strain) in the same way, the $MIC_{50}$ value of arenicolide A was about 6.9 μM.

Therefore, arenicolide A was confirmed to have anti-tuberculosis activity.

2-2. Confirmation of Anti-BCG Activity of Arenicolide

It was confirmed whether the arenicolide compound has an effective inhibitory activity against BCG (*bacillus* Calmette-Guerin) strain, that is, *Mycobacterium bovis*.

As described in Example 2-1, 57BL/6 mice were nasally infected with $1\times10^6$/CFU of BCG strain. From the 4th day, arenicolide A or arenicolide C was orally administered at a dose of 100 mg/body weight kg for 6 days. As a negative control, 2.5% (v/v) DMSO and 2.5% (v/v) ethanol were administered. Mice were sacrificed on day 10 from the day of infection. The number of viable tubercle bacilli in the lung tissue was investigated, and the results are shown in FIG. 3 (each, n=6, : p<0.01, *: p<0.001).

Figure 3:
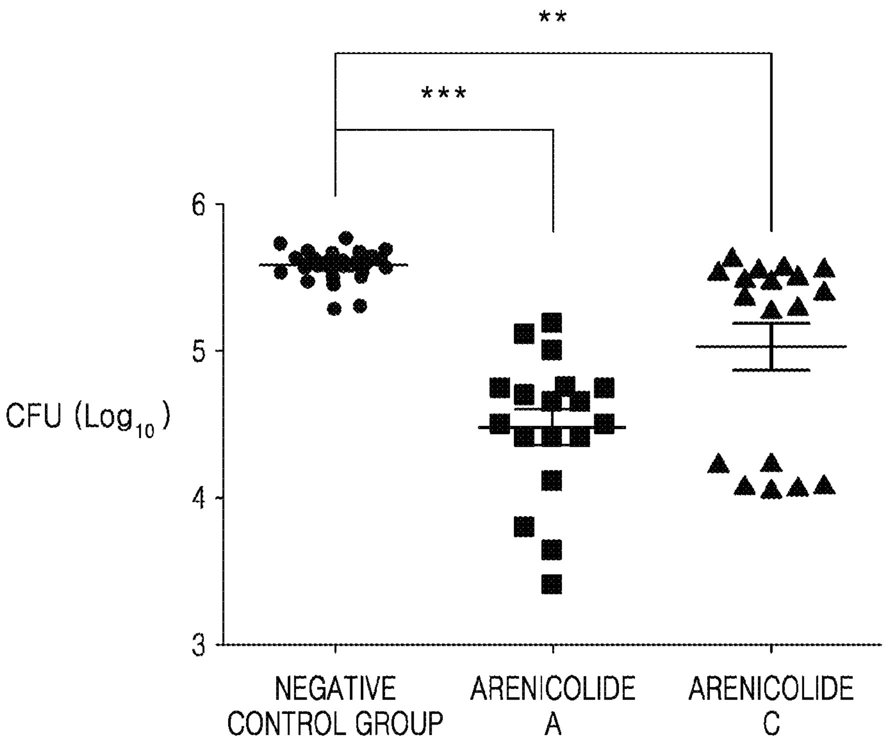
FIG. 3 is a graph showing the number of viable cells of a BCG strain in lung tissue when arenicolide A or arenicolide C is administered (CFU: colony forming unit).

As shown in FIG. 3, it was confirmed that arenicolide A and arenicolide C had effective inhibitory activity against BCG bacteria compared to the negative control.

2-3. Confirmation of Anti-Atypical Tubercle Bacilli Activity of Arenicolide

It was confirmed whether the arenicolide compound has an effective inhibitory activity against *Mycobacterium abscessus*, atypical tubercle bacilli.

As described in Example 2-2, 57BL/6 mice were nasally infected with $1\times10^7$/CFU of *M. abscessus* strain. From the 3rd day, arenicolide A was orally administered at a dose of 100 mg/body weight kg for 5 days. As a negative control, 2.5% (v/v) DMSO and 2.5% (v/v) ethanol were administered. Mice were sacrificed on day 7 from the day of infection. The number of viable tubercle bacilli in the lung tissue was investigated, and the results are shown in FIG. 3 (each, n=6, ***: $p<0.001$).

Figure 4:
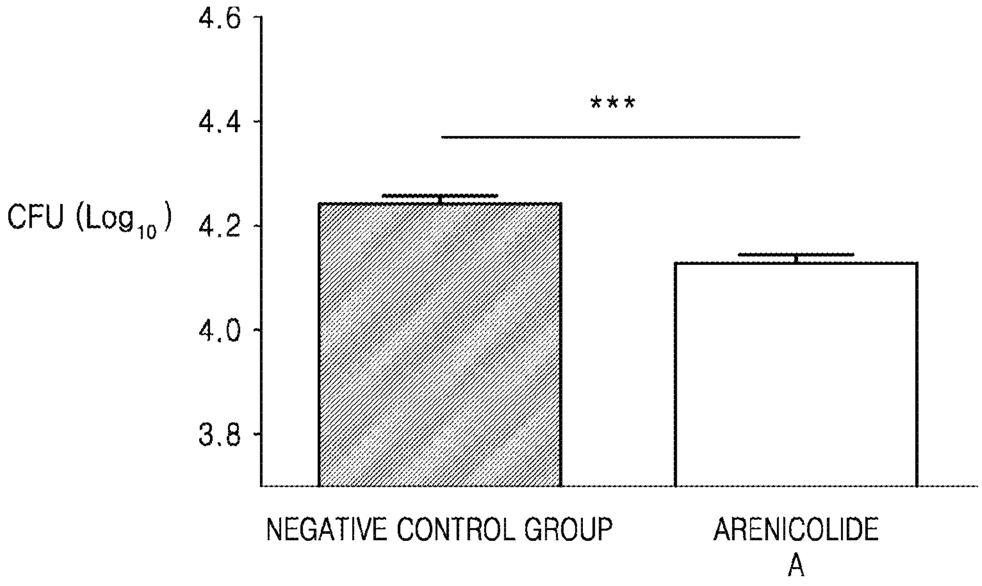
FIG. 4 is a graph showing the number of viable cells of an *M. abscessus* strain in lung tissue when arenicolide A is administered (CFU: colony forming unit).

As shown in FIG. 4, the number of viable cells in the lung tissue was significantly decreased in the group to which arenicolide A was orally administered compared to the negative control group. Arenicolide A was confirmed to be effective as a therapeutic candidate in a mouse non-tuberculous *Mycobacterium* infection model.

2-4. Evaluation of Effectiveness of Combined Administration of Arenicolide and Anti-Tuberculosis Drugs The effect by the combined administration was confirmed when arenicolide and an anti-tuberculosis drug were combined.

Specifically, *M. tuberculosis* was cultured at 37° C. in Middlebrook 7H9 medium to which ADC was added. A 100 μl of medium aliquot was added to each well of a 96-well microtiter plate, and two-fold serial dilutions of arenicolide A or ethambutol were added directly to each well. The plates were then incubated at 37° C. for 5 days. Resazurin (0.025% (w/v)) was added to each well, and fluorescence intensity was measured by using a SpectraMax® M3 Multi-Mode Microplate Reader (Molecular Devices, CA, USA) (ex/em 560/590 nm). MIC values were calculated by using Prism 6 (GraphPad Software, Inc., La Jolla, CA). Fluorescence intensities of different concentrations of arenicolide and ethambutol are shown in FIG. 5A.

Meanwhile, *Mycobacterium tuberculosis* was cultured in a solid medium containing arenicolide and ethambutol combined at each MIC. In order to read the survival of the bacteria, *Mycobacterium tuberculosis* was inoculated into a solid medium (7H10 added), and the growth of the bacteria was measured after culturing at 37° C. for 3 weeks. An image of the cultured bacteria is shown in FIG. 5B.

Figure 5A:
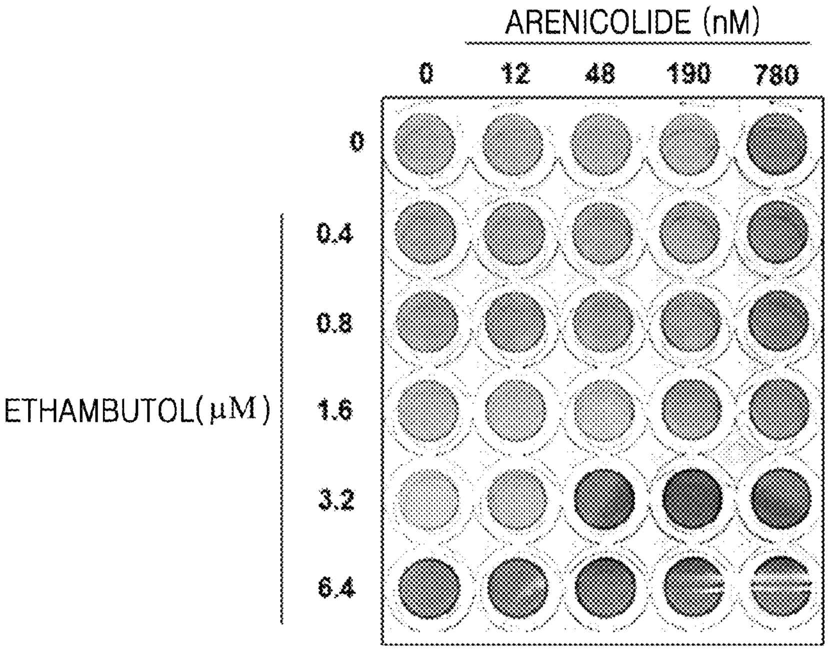
FIG. 5A is a fluorescence image showing the inhibition of growth of *Mycobacterium tuberculosis* according to concentrations of arenicolide A and ethambutol.
Figure 5B:
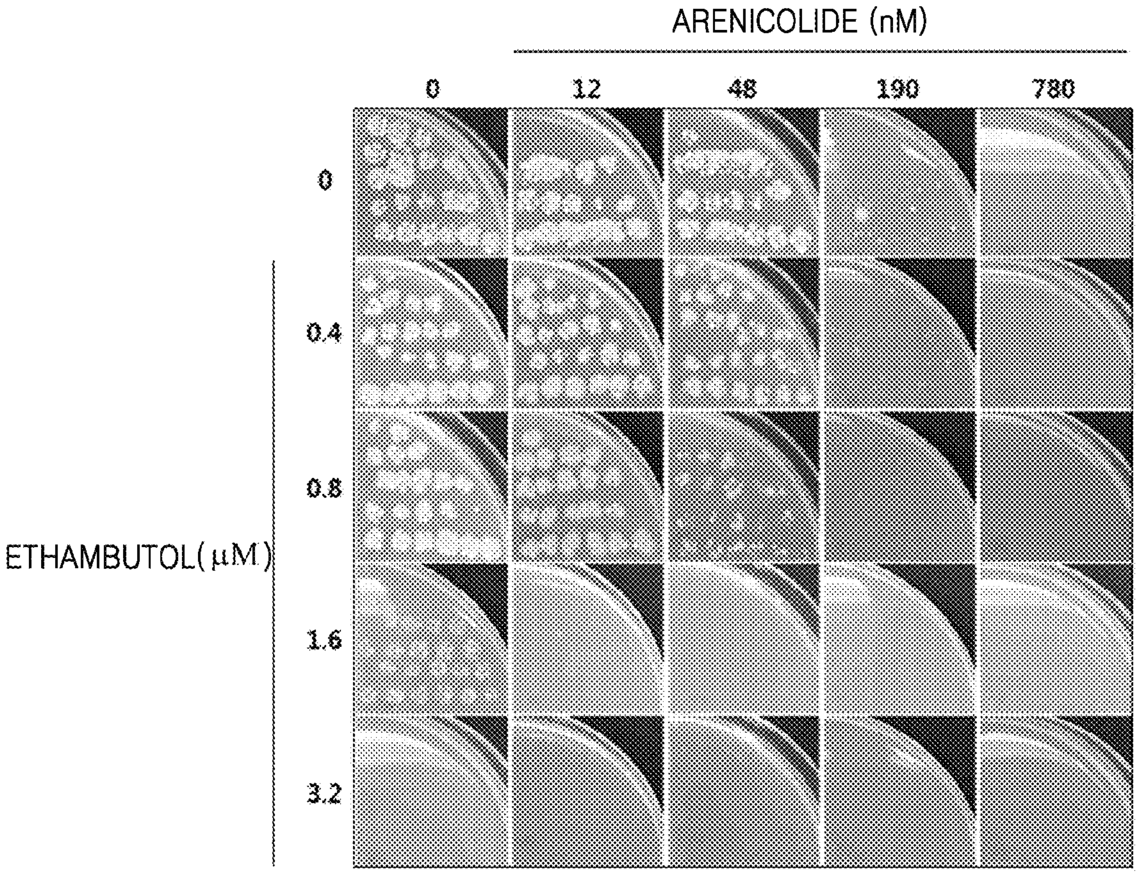
FIG. 5B is an image of *Mycobacterium tuberculosis* cultured in a solid medium containing arenicolide A and ethambutol.

As shown in FIGS. 5A and 5B, it was confirmed that the combination of arenicolide A and ethambutol acts synergistically against *Mycobacterium tuberculosis*. In particular, it was confirmed that colonies of *Mycobacterium tuberculosis* were not formed in the combination of 1.6 μM of ethambutol and 0.048 μM of arenicolide A and in the combination of 0.8 μM of ethambutol and 0.19 μM of arenicolide A. Through this, it was confirmed that the MIC value of ethambutol, which was administered in combination, may be lowered to about ¼ when a small amount of arenicolide A was administered. In addition, it was confirmed that, when administered alone, arenicolide A (MIC=0.78 μM) has superior efficacy compared to ethambutol (MIC=3.2 μM), a positive control drug.

The invention claimed is:

1. A method of treating *Mycobacterium* sp. bacterial infection or symptoms related thereto, comprising administering to a subject the pharmaceutical composition comprising a compound or a stereoisomer, solvate, or pharmaceutically acceptable salt thereof, wherein the compound is represented by Formula 1:

[Formula 1]

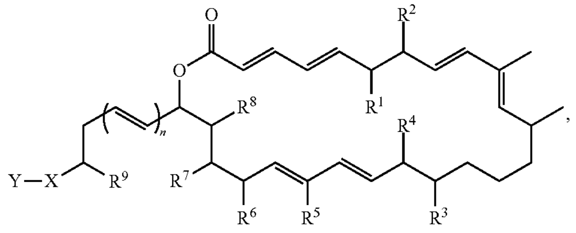

wherein in Formula 1, $R^1$, $R^2$, $R^3$, $R^4$, $R^7$, $R^8$, and $R^9$ are each independently selected from hydrogen, a hydroxyl group, an amino group, a halogen group, a ketone group, a cyano group, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, or a combination thereof, $R^5$ and $R^6$ are each independently hydrogen, a hydroxyl group, an amino group, a halogen group, a cyano group, —C(═O)$R_a$, —C(═O)O$R_a$, —OCO(O$R_a$), —C═N($R_a$), —S$R_a$, —S(═O)$R_a$, —S(═O)$_2R_a$, —P$R_a$, a substituted or unsubstituted $C_1$ to $C_{20}$ alkyl group, a substituted or unsubstituted $C_1$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, wherein $R_a$ is hydrogen, a $C_1$ to $C_{10}$ alkyl group, or a $C_6$ to $C_{20}$ aryl group, n is an integer from 1 to 20, X is a substituted or unsubstituted 3-membered to 10-membered heterocyclic ring group containing one or more O, and the substituted heterocyclic ring group is substituted with a hydroxyl group, a $C_1$ to $C_{10}$ alkyl group, a $C_1$ to $C_{10}$ alkoxy group, or a combination thereof, and Y is a substituted or unsubstituted $C_1$ to $C_{30}$ alkyl group, and the substituted alkyl group is substituted with one or more hydroxyl groups or $C_1$ to $C_{10}$ alkoxy groups.

2. The method of claim 1, further comprising administering an antibiotic to the subject.

3. The method of claim 1, wherein at least one of $R^1$, $R^3$, and $R^8$ is a substituted or unsubstituted $C_1$ to $C_{10}$ alkoxy group.

4. The method of claim 3, wherein at least one of $R^1$, $R^3$, and $R^8$ is a methoxy group.

5. The method of claim 1, wherein at least one of $R^2$, $R^4$, $R^7$, and $R^9$ is a hydroxyl group.

6. The method of claim 1, wherein at least one of $R^5$ and $R^6$ is a methyl group.

7. The method of claim 1, wherein the heterocyclic ring group in X is an ethylene oxide group or tetrahydrofuran.

8. The method of claim 1, wherein the compound represented by Formula 1 is represented by Formula 2 or Formula 3:

Formula 2
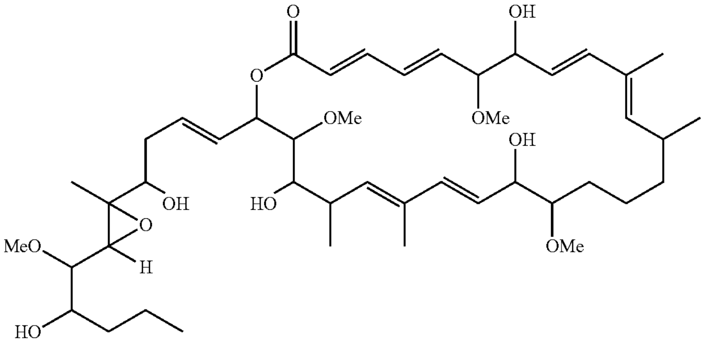
and;
Formula 3
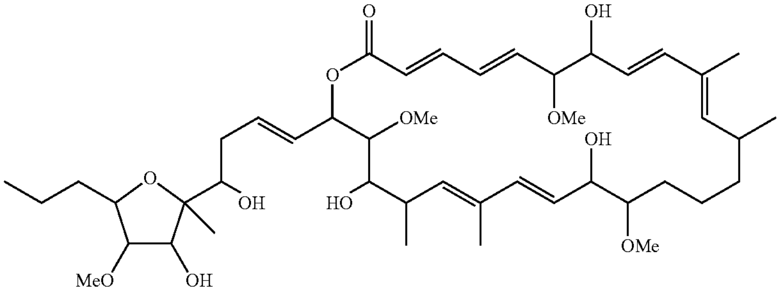
.
9. The method of claim 1, wherein the compound represented by Formula 1 is represented by Formula 4 or Formula 5:
Formula 4
Formula 4
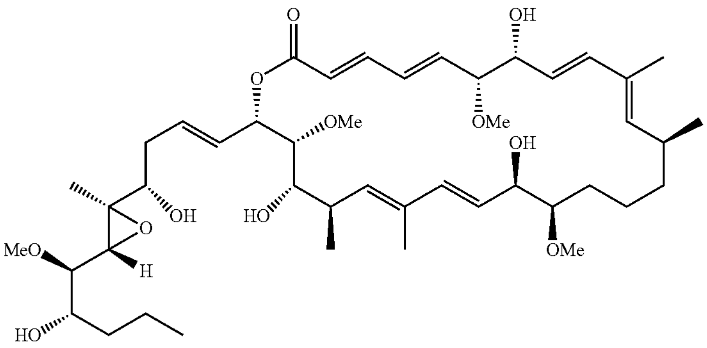
and;
Formula 5
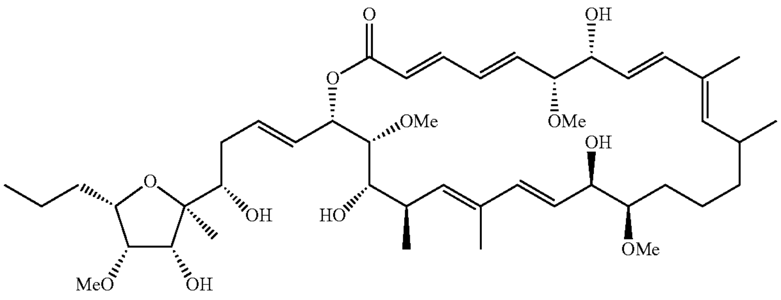
.
10. The method of claim 1, wherein the *Mycobacterium* sp. bacterial infection is selected from the group consisting of tuberculosis, Hansen's disease, and nontuberculous mycobacterial (NTM) infection.

11. The method of claim 1, wherein the bacteria of the *Mycobacterium* sp. is selected from the group consisting of *Mycobacterium tuberculosis*, nontuberculous mycobacteria, and a BCG strain.

12. The method of claim 1, wherein the bacteria of the *Mycobacterium* sp. is selected from the group consisting of *Mycobacterium tuberculosis, Mycobacterium bovis, Mycobacterium abscessus, Mycobacterium africanum, Mycobacterium microti, Mycobacterium leprae, Mycobacterium canetti, Mycobacterium avium, Mycobacterium kansasii*, and *Mycobacterium marinum.*

13. The method of claim 2, wherein the antibiotic is an anti-tuberculosis drug.

14. The method of claim 13, wherein the anti-tuberculosis drug is ethambutol, isoniazid, rifampicin, SQ-109, pyrazinamide, streptomycin, kanamycin, capreomycin, ethionamide, prothionamide, enviomycin, para-aminosalicylic acid, cycloserine, amikacin, levofloxacin, moxifloxacin, gatifloxacin, ofloxacin, terizidone, thionamide, ethionamide, prothionamide, clofazimine, linezolid, amoxicillin, clavulanate, thioacetazone, imipenem, cilastatin, clarithromycin, bedaquiline, delamanid, limipenem, cilastatin, meropenem, or a combination thereof.

* * * * *